(12) United States Patent  (10) Patent No.: US 8,177,839 B2
Koob et al.  (45) Date of Patent: May 15, 2012

(54) WOVEN AND/OR BRAIDED FIBER IMPLANTS AND METHODS OF MAKING SAME

(75) Inventors: Thomas J. Koob, Tampa, FL (US); Tian Davis, Bradenton, FL (US); Douglas Pringle, Brandon, FL (US)

(73) Assignee: Shriners Hospitals for Children, Tampa, FL (US)

( * ) Notice: Subject to any disclaimer, the term of this patent is extended or adjusted under 35 U.S.C. 154(b) by 169 days.

(21) Appl. No.: 11/964,745

(22) Filed: Dec. 27, 2007

(65) Prior Publication Data

US 2008/0188933 A1  Aug. 7, 2008

Related U.S. Application Data

(60) Provisional application No. 60/882,065, filed on Dec. 27, 2006, provisional application No. 60/883,408, filed on Jan. 4, 2007, provisional application No. 60/890,660, filed on Feb. 20, 2007.

(51) Int. Cl.
*A61F 2/08* (2006.01)
*A61B 19/02* (2006.01)
*D04C 1/06* (2006.01)

(52) U.S. Cl. ............... 623/13.11; 623/13.12; 623/13.19; 206/570; 87/9

(58) Field of Classification Search ....... 623/13.11–13.2
See application file for complete search history.

(56) References Cited

U.S. PATENT DOCUMENTS

| | | | |
|---|---|---|---|
| 3,316,699 A | 5/1967 | Mattingly | |
| 4,590,928 A * | 5/1986 | Hunt et al. | 606/916 |
| 4,792,336 A | 12/1988 | Hlavacek et al. | 623/13 |
| 4,841,962 A | 6/1989 | Berg et al. | |
| 4,883,486 A | 11/1989 | Kapadia et al. | |
| 4,979,956 A * | 12/1990 | Silvestrini | 623/13.11 |
| 5,078,744 A | 1/1992 | Chvapil | |
| 5,106,949 A | 4/1992 | Kemp et al. | |
| 5,256,418 A | 10/1993 | Kemp et al. | |
| 5,263,984 A | 11/1993 | Li et al. | |
| 5,378,469 A | 1/1995 | Kemp et al. | |
| 5,569,302 A | 10/1996 | Proto et al. | |
| 5,656,605 A | 8/1997 | Hansson et al. | |
| 5,713,374 A | 2/1998 | Pachence et al. | 128/898 |

(Continued)

FOREIGN PATENT DOCUMENTS

CA  2285161  4/2001

(Continued)

OTHER PUBLICATIONS

Brunelli et al., Slip-knot flexor tendon suture in zone II allowing immediate mobilisation, The Hand, 1983, vol. 15, pp. 352-358.

(Continued)

*Primary Examiner* — David Isabella
*Assistant Examiner* — Yashita Sharma
(74) *Attorney, Agent, or Firm* — Myers Bigel Sibley & Sajovec, P.A.

(57) ABSTRACT

Bioprosthesis having an implantable braided or woven construct with a plurality of collagen-derived fibers interlocked or interlaced together. The braided or woven constructs can be flexible and resorbable. The braided or woven constructs can have the dynamic flexibility, tensile strength and stiffness suitable for tendon or ligament repairs. The braided or woven construct may be used for ulnar collateral ligament reconstruction.

43 Claims, 12 Drawing Sheets

U.S. PATENT DOCUMENTS

| | | | |
|---|---|---|---|
| 5,718,012 | A | 2/1998 | Cavailaro |
| 5,718,717 | A | 2/1998 | Bonutti |
| 6,090,117 | A | 7/2000 | Shimizu |
| 6,224,630 | B1 | 5/2001 | Bao et al. |
| 6,277,397 | B1 | 8/2001 | Shimizu |
| 6,280,474 | B1 | 8/2001 | Cassidy et al. |
| 6,292,697 | B1 * | 9/2001 | Roberts .......................... 607/27 |
| 6,335,007 | B1 | 1/2002 | Shimizu et al. |
| 6,531,147 | B2 | 3/2003 | Sawhney et al. |
| 6,565,960 | B2 | 5/2003 | Koob et al. ................. 428/304.4 |
| 6,589,257 | B1 | 7/2003 | Shimizu |
| 6,592,623 | B1 | 7/2003 | Bowlin et al. |
| 6,645,247 | B2 | 11/2003 | Ferree |
| 6,692,528 | B2 | 2/2004 | Ward et al. |
| 6,713,537 | B1 | 3/2004 | Ueda et al. |
| 6,716,234 | B2 | 4/2004 | Grafton et al. |
| 6,730,124 | B2 | 5/2004 | Steiner |
| 6,821,530 | B2 | 11/2004 | Koob et al. ................... 424/458 |
| 6,866,681 | B2 | 3/2005 | Laboureau et al. |
| 6,936,072 | B2 | 8/2005 | Lambrecht et al. |
| 6,955,683 | B2 | 10/2005 | Bonutti |
| 6,994,719 | B2 | 2/2006 | Grafton |
| 7,029,490 | B2 | 4/2006 | Grafton et al. |
| 7,084,082 | B1 | 8/2006 | Shimizu |
| 7,090,690 | B2 | 8/2006 | Foerster et al. |
| 7,115,146 | B2 | 10/2006 | Boyer et al. |
| 7,135,040 | B2 | 11/2006 | Wang et al. |
| 7,309,359 | B2 | 12/2007 | Trieu et al. |
| 7,354,627 | B2 | 4/2008 | Pedrozo et al. |
| 7,650,742 | B2 | 1/2010 | Ushijima |
| 2001/0018619 | A1 | 8/2001 | Enzerink et al. |
| 2002/0037940 | A1 | 3/2002 | Koob et al. |
| 2002/0123805 | A1 | 9/2002 | Murray et al. |
| 2003/0100108 | A1 | 5/2003 | Altman et al. |
| 2003/0230316 | A1 | 12/2003 | Glucksman et al. |
| 2004/0110439 | A1 | 6/2004 | Chaikof et al. |
| 2004/0131562 | A1 | 7/2004 | Gower et al. |
| 2004/0193241 | A1 | 9/2004 | Stinson |
| 2004/0224406 | A1 | 11/2004 | Altman et al. |
| 2004/0267362 | A1 | 12/2004 | Hwang et al. |
| 2005/0192631 | A1 | 9/2005 | Grafton |
| 2006/0095134 | A1 | 5/2006 | Trieu et al. |
| 2006/0257377 | A1 | 11/2006 | Atala et al. |
| 2006/0263417 | A1 | 11/2006 | Lelkes et al. |
| 2007/0118217 | A1 | 5/2007 | Brulez et al. |
| 2007/0248643 | A1 | 10/2007 | Devore et al. |
| 2008/0020012 | A1 | 1/2008 | Ju et al. |
| 2008/0038352 | A1 | 2/2008 | Simpson et al. |
| 2008/0124371 | A1 | 5/2008 | Turos et al. |
| 2008/0161917 | A1 | 7/2008 | Koob et al. |
| 2008/0200992 | A1 | 8/2008 | Koob et al. |
| 2008/0215150 | A1 | 9/2008 | Koob et al. |
| 2008/0300683 | A1 | 12/2008 | Altman et al. |
| 2009/0216233 | A1 | 8/2009 | Wiedrich et al. |
| 2009/0287308 | A1 | 11/2009 | Davis et al. |

FOREIGN PATENT DOCUMENTS

| | | |
|---|---|---|
| EP | 1493404 | 1/2005 |
| WO | WO 96/14095 | 5/1996 |
| WO | WO 9614095 A1 * | 5/1996 |
| WO | WO 01-72241 | 10/2001 |
| WO | WO2008/041183 | 4/2008 |

OTHER PUBLICATIONS

Greis et al, The influence of tendon length and fit on the strength of the tendon-bone tunnel complex, Am. J. Sports Med., 2001, 29:493-497.

Becker et al., Early active motion following a beveled technique of flexor tendon repair: Report on fifty cases, Journal of Hand Surgery, 1979, vol. 4 No. 5, pp. 454-460.

Koob et al., Biomimetic approaches to tendon repair, Comp. Biochem. Physiol. A Mol. Integr. Phys., 2002, 133: 1171-1192.

Koob et al., Material properties of NDGA-collagen composite fibers: development of biologically based tendon constructs, Biomaterials, 2002, 23:202-212.

Koob et al., Mechanical and thermal properties of novel polymerized NDGA-gelatin hydrogels, Biomaterials, 2003, 24:1285-1292.

Messina, The double armed suture: Tendon repair with immediate mobilization of the fingers, Journal of Hand Surgery, 1992, 17A:137-142.

Powell et al., Forces transmitted along human flexor tendons during passive and active movements of the fingers, J. Hand Surg., 2004, 29:4:386-389.

Rodeo et al., Tendon healing in a bone tunnel. A biomechanical and histological study in a dog, J. Bone Joint Surg., 1993, 75:1795-1803.

Savage et al., Flexor tendon repair using a "six strand" method of repair and early active mobilisation, Journal of Hand Surgery, (British vol. 1989), 14B:396-399.

Silva et al., The insertion site of the canine flexor digitorum profundus tendon heals slowly following injury and suture repair, J. Ortho. Res., 2002, 20:447-453.

Trotter et al., Molecular structure and functional morphology of echinoderm collagen fibrils, Cell Tiss. Res., 1994, 275: 451-458.

International Search Report and Written Opinion for corresponding PCT application No. PCT/US2007/026381; Date of mailing Apr. 23, 2009.

Grog, The Reef (Square) Knot, Animated Knots by Grog, downloaded at http://www.animatedknots.com/reef/index.php, on May 28, 2009 using WayBack Machine on www.archive.org for publication date of Dec. 26, 2005.

Koob et al., Biocompatibility of NDGA-polymerized collagen fibers. I. Evaluation of cytotoxicity with tendon fibroblasts in vitro, © 2001John Wiley & Sons, Inc.

Koob et al., Biocompatibility of NDGA-polymerized collagen fibers. II. Attachment, proliferation, and migration of tendon fibroblasts in vitro, @ 2001John Wiley & Sons, Inc.

Martin et al., Anterior Cruciate Ligament Graft Preparation: A New and Quick Alternative to the Whipstitch, Arthroscopy: The Journal of Arthroscopic & Related Surgery, Online Publication Date of Nov. 29, 2006.

Nottage et al., Arthoscopic Knot Tying Techniques, Arthroscopy: The Journal of Arthroscopic & Related Surgery 15(1999): 515-521.

Product advertisement, Conair QB3ECS Quick Braid Styling Kit, © 2007 (1 page).

Integra™ NeuraGen™ Nerve Guide, Product Broacher, 4 pages 2005.

Integra™ NeuraGen™ Nerve Guide, Product Webpage, http://www.integra-ls.com/products/?product=88, Date unknown but believed to be prior to the filing date of the present application, 2 pages.

Integra™ NeuraWrap™ Nerve Protector, Product Webpage, http://www.integra-ls.com/products/?products=198, Date unknown but believed to be prior to the filing date of the present application, 2 pages.

* cited by examiner

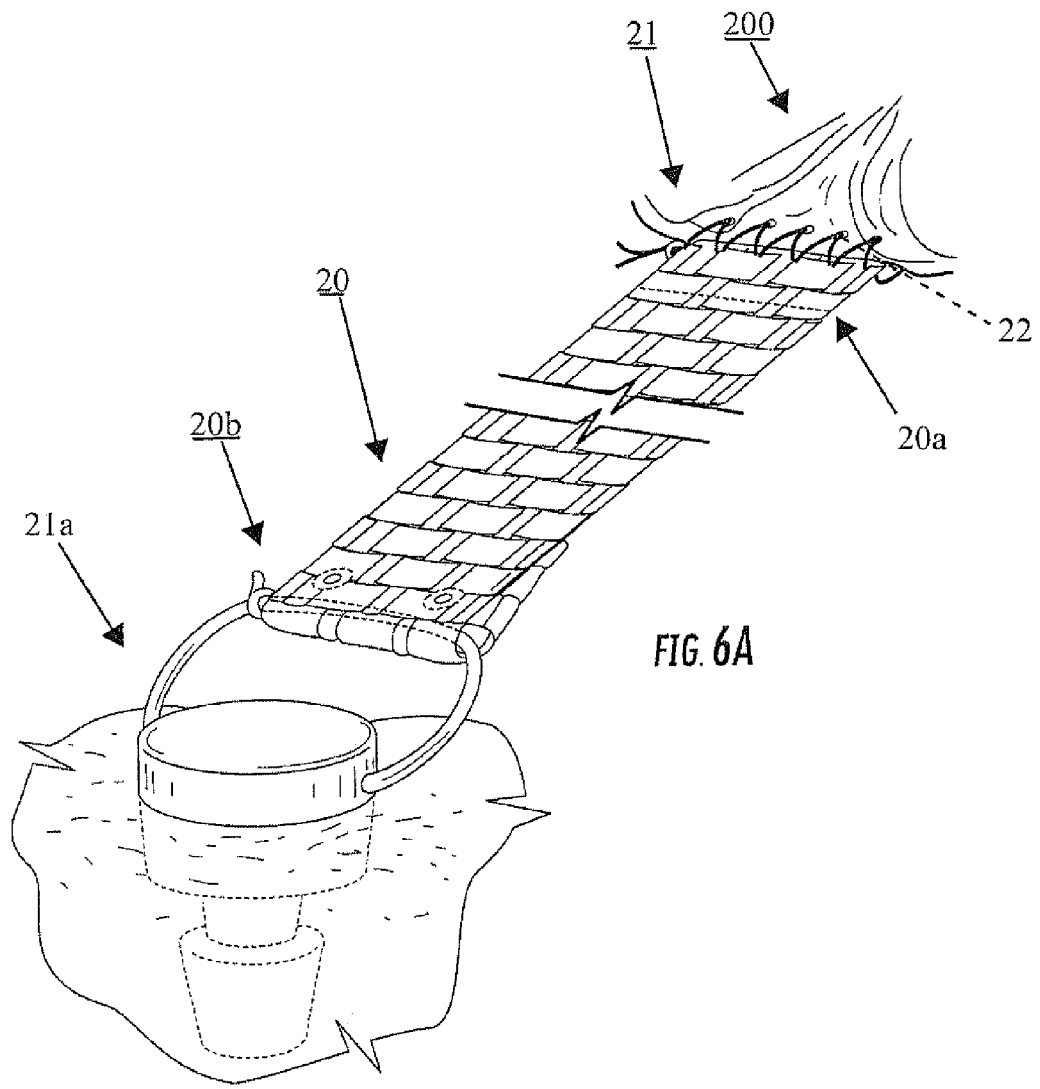

| Round braided | strand number | | | | | | | | |
|---|---|---|---|---|---|---|---|---|---|
| 0 | 1 | 2 | 3 | 4 | 5 | 6 | 7 | 8 | 9 |
| 1 | 2 | 3 | 4 | _5_ | 6 | 1 | 8 | 9 | 7 |
| 2 | 3 | 4 | 2 | 6 | 1 | 8 | 9 | 7 | _5_ |
| 3 | 4 | 2 | 6 | _1_ | 8 | 3 | 7 | 5 | 9 |
| 4 | 2 | 6 | 4 | 8 | 3 | 7 | 5 | 9 | _1_ |
| 5 | 6 | 4 | 8 | _3_ | 7 | 2 | 9 | 1 | 5 |
| 6 | 4 | 8 | 6 | 7 | 2 | 9 | 1 | 5 | _3_ |
| 7 | 8 | 6 | 7 | _2_ | 9 | 4 | 5 | 3 | 1 |
| 8 | 6 | 7 | 8 | 9 | 4 | 5 | 3 | 1 | _2_ |
| 9 | 7 | 8 | 9 | _4_ | 5 | 6 | 1 | 2 | 3 |
| 10 | 8 | 9 | 7 | 5 | 6 | 1 | 2 | 3 | _4_ |
| 11 | 9 | 7 | 5 | _6_ | 1 | 8 | 3 | 4 | 2 |
| 12 | 7 | 5 | 9 | 1 | 8 | 3 | 4 | 2 | _6_ |
| 13 | 5 | 9 | 1 | _8_ | 3 | 7 | 2 | 6 | 4 |
| 14 | 9 | 1 | 5 | 3 | 7 | 2 | 6 | 4 | _8_ |
| 15 | 1 | 5 | 3 | _7_ | 2 | 9 | 4 | 8 | 6 |
| 16 | 5 | 3 | 1 | 2 | 9 | 4 | 8 | 6 | _7_ |
| 17 | 3 | 1 | 2 | _9_ | 4 | 5 | 6 | 7 | 8 |
| 18 | 1 | 2 | 3 | 4 | 5 | 6 | 7 | 8 | _9_ |

BRAIDED NDGA-COLLAGEN RIBBONS FOR LIGAMENT REPAIR

81-FIBER BRAIDED RIBBON

US 8,177,839 B2

WOVEN AND/OR BRAIDED FIBER IMPLANTS AND METHODS OF MAKING SAME

RELATED APPLICATION

This application claims the benefit of priority of U.S. Provisional Application Ser. No. 60/882,065, Filed Dec. 27, 2006, and U.S. Provisional Application Ser. No. 60/883,408, Filed Jan. 4, 2007, and U.S. Provisional Application No. 60/890,660, filed Feb. 20, 2007, the contents of which are hereby incorporated by reference as if recited in full herein.

FIELD OF THE INVENTION

The invention relates to implantable prostheses.

BACKGROUND OF THE INVENTION

It is believed that the linear organization of natural collagen fibers in tendons results in optimal stiffness and strength at low strains under tensile loads. However, this organization makes repairing ruptured or lacerated tendons difficult. Current suturing techniques to join split ends of tendons, while providing sufficient mechanical strength to prevent gapping, are often inadequate to carry normal loads and may not ever allow the tendon to regain original mechanical properties or mobility. Immobilization protocols used to restore tendon congruity may result in scar formation at the repair site and peripheral adhesions that can limit excursions. One or more similar issues may be associated with conventional ligament repair techniques.

SUMMARY OF EMBODIMENTS OF THE INVENTION

Embodiments of the present invention are directed to implantable biocompatible prostheses that provide new and alternative surgical treatments of tissue.

In some embodiments, the implantable bioprostheses have a construct with a plurality of fibers braided and/or woven together.

In some embodiments, the fibers can comprise nordihydroguaiaretic acid (NDGA)-treated polymer fibers. The construct may have a substantially flat ribbon configuration sized and configured to define a ligament bioprosthesis. In other embodiments, the construct may have a substantially tubular rope configuration sized and configured to define a tendon bioprosthesis.

Other embodiments are directed to methods of making a bioprosthesis. The methods include: (a) providing a plurality of discrete bundles of fibers; and (b) braiding or weaving the bundles into an interlocking pattern to form a bioprosthesis construct.

In some embodiments, the fibers can comprise NDGA-polymerized collagen fibers. In some embodiments, the plurality of discrete bundles of fibers are arranged to be substantially parallel to each other in a respective bundle. The interlocking pattern can form a substantially flat bioprosthesis construct. In other embodiments, the interlocking pattern forms a substantially tubular bioprosthesis construct.

Yet other embodiments are directed to a medical kit for a tendon or ligament repair, augmentation or replacement. The kit includes: (a) a braided NDGA collagen fiber construct; and (b) a sterile package sealably enclosing the braided or woven fiber construct therein.

Further features, advantages and details of the present invention will be appreciated by those of ordinary skill in the art from a reading of the figures and the detailed description of the embodiments that follow, such description being merely illustrative of the present invention.

BRIEF DESCRIPTION OF THE DRAWINGS

FIG. 6A is a schematic illustration of a braided construct in position in the body of a patient according to embodiments of the invention.

FIG. 8A is a graph of strain at failure of NDGA fibers of different fibers showing strain versus test rate in mm/sec.

DETAILED DESCRIPTION

Figure 1:
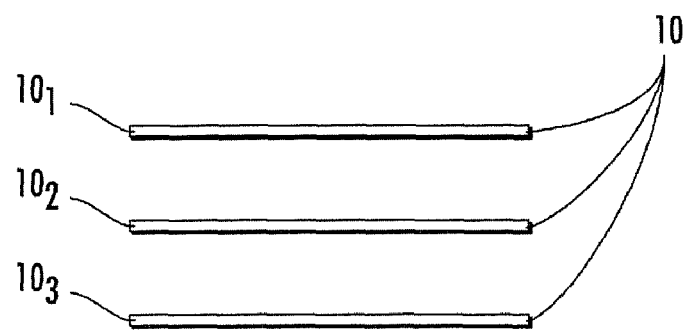
FIG. 1 is a schematic illustration of bundles used to form a braided construct according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The terms "implant" and "prosthesis" and "construct" are used interchangeably herein to designate an implantable product configured to repair or replace (at least a portion of) a natural tendon, ligament or other tissue of a mammalian subject (for veterinary or medical (human) applications). The term "implantable" means the device can be inserted, embedded, grafted or otherwise chronically attached or placed on or in a patient.

Collagen "microfibrils," "fibrils," "fibers," and "natural fibers" refer to naturally-occurring structures found in a tendon. Microfibrils are about 3.5 to 50 nm in diameter. Fibrils are about 50 nm to 50 µm in diameter. Natural fibers are above 50 µm in diameter. A "synthetic fiber" refers to any fiber-like material that has been formed and/or chemically or physically created or altered from its naturally-occurring state. For example, an extruded fiber of fibrils formed from a digested tendon is a synthetic fiber but a tendon fiber newly harvested from a mammal is a natural fiber. Of course, synthetic collagen fibers can include non-collagenous components, such as particulates, hydroxyapatite and other mineral phases, or drugs that facilitate tissue growth. See, U.S. Pat. No. 6,821, 530, hereby incorporated by reference herein. For example, the compositions can contain carbon nano-tubes, zinc nano-wires, nano-crsytalline diamond, or other nano-scale particulates; larger crstalline and non-crystalline particulates such as calcium phosphate, calcium sulfate, apatite minerals. For example, the fibers and/or constructs formed of the fibers can include compositions can contain therapeutic agents such as bisphosphonates, anti-inflammatory steroids, growth factors such as basic fibroblast growth factor, tumor growth factor beta, bone morphogenic proteins, platelet-derived growth factor, and insulin-like growth factors; chemotactic factors such fibronectin and hyaluronan; and extracellular matrix molecules such as aggrecan, biglycan, and decorin. In some embodiments, the fibers and/or constructs can contain cells, engineered cells, stem cells, and the like, as well as combinations of the above.

The term "suture" refers to a flexible elongate material that is used to attach the bioprothesis to a target anatomical structure to help hold the bioprosthesis in location in the body. The suture may be resorbable or non-resorbable, synthetic or natural. The suture can be configured to hold the implant in location for at least an initial post-implantation period of at least about 1 week, but may reside permanently in the body or, as noted above, may be substantially resorbable over time. The suture can be a single filament or multi-filament (braided) thread, floss, gut or wire, or combinations thereof that can be used to hold a portion of an implant against or attached to target structures, typically to bone and/or tissue. The suture may comprise a resorbable or non-resorbable biocompatible material. Examples of suture materials include elastomeric materials, such as, for example, polymers, copolymers and/or derivatives thereof, including Vicryl®, as well as other materials including, for example, NITINOL, and combinations thereof. The suture may be used to with a suture anchor (bone or tissue anchor).

The term "atraumatic" with respect to suture needles with thread refers to an atraumatic or eyeless needle attached to a specific length of suture material (thread or filament). The suture and needle are preformed and purchased as a unit, as the suture needle manufacturer swages or binds the suture thread to the eyeless atraumatic needle at the factory. In a conventional traumatic needle with suture, the thread comes out of the needle's hole or eye on both sides. When passing through the tissues, this type of suture may rip tissue, at least to a certain extent. In contrast to the conventional "trauma"-type needle with suture, the atraumatic needle with suture does not cause trauma (hence the name "atraumatic"). Because of these advantages, atraumatic needles with sutures are today very widely used.

As with conventional sutures, the sutures of atraumatic needles can be absorable or non-absorable. As is well known, there are several shapes of atraumatic needles, including straight, half curved, one-third curved and others. The body of the needle is available also in different makes, like circular, with edge on the outer side, with edge on the inner side, and others.

The term "flexible" means that the so-called member can be flexed or bent.

The terms "braided" and "woven" and derivatives thereof mean to braid and/or (inter)weave, interlace and/or interlock in any manner, a plurality, typically three or more, fibers or bundles of fibers together, including manually or automatically weaving, braiding, knitting and/or knotting and combinations of these or other interlocking or interlaced constructions. The woven constructs may comprise a plurality of warp and weft fibers.

Figure 2:
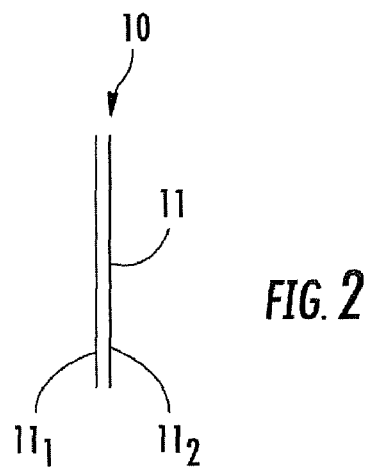
FIG. 2 is a schematic illustration of a multi-fiber bundle according to embodiments of the invention.
Figure 4B:
FIG. 4B is a side view of one configuration of the construct shown in FIG. 4A according to some embodiments of the invention.
Figure 4A:
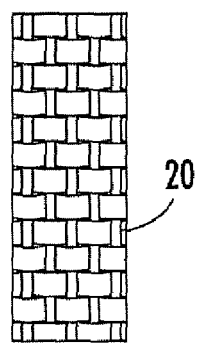
FIG. 4A is a top view of a schematic illustration of a biocompatible bioprosthesis having a braided constructs according to embodiments of the invention.
Figure 4C:
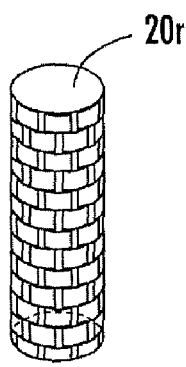
FIG. 4C is a side perspective view of another configuration of the construct shown in FIG. 4A according to other embodiments of the invention.

FIG. 1 is a schematic illustration of a plurality of fiber bundles 10 that can be woven or braided together to form a braided/woven implantable bioprosthesis construct 20 (FIGS. 4A-4C). As shown, the plurality of bundles of fibers 10 is at least three bundles, $10_1$, $10_2$, $10_3$. As shown in FIG. 2, each bundle 10 can include a plurality of fibers, shown for example as two fibers $11_1$, $11_2$. The number of fibers 11 and the number of bundles 10 can vary depending on the mechanical properties and shape desired.

Figure 3:
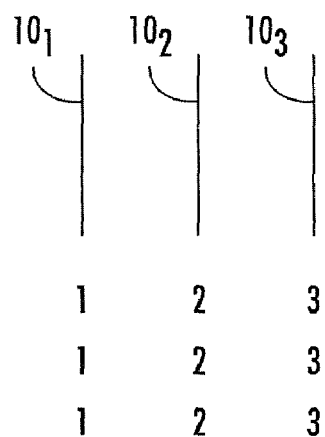
FIG. 3 is a schematic illustration of a braid pattern that can be used to form an implantable biocompatible bioprosthesis according to embodiments of the invention.

As shown in FIG. 3, the construct 20 (FIGS. 4A-4C) may have a substantially regular braid or weave pattern, shown, for example, with a repeating order of strand 1, 2, 3. Alternatively, the construct 20 may be formed using an irregular braid or weave pattern (not shown), or combinations of both over the length of the construct.

In some embodiments, the plurality of bundles 10 is between about six to about twenty-seven and the plurality of fibers 11 in at least some of the bundles 10 is between about six to about eleven fibers. Lesser and greater numbers of bundles and fibers may be used and different numbers of fibers 11 may be used in some bundles 10.

FIG. 4A is a top view of a schematic illustration of an exemplary braided construct 20. The construct 20 can be configured as a substantially flat or planar construct 20$f$ (also described as a "ribbon" construct) as shown in FIG. 4B or as a substantially tubular or rope-like construct 20$r$ as shown in FIG. 4C. The construct 20$f$ shown in FIG. 4B may be particularly suitable for a ligament prosthesis, such as for an Anterior Cruciate Ligament (ACL) repair or replacement. The construct 20$r$ shown in FIG. 4C may be particularly suitable as a tendon-prosthesis, such as, for example, the flexor tendon. Other braid configurations may also be used as suitable for the target treatment site/prosthesis. The rope configuration 20$r$ can be woven and/or braided so that the fibers occupy the core (i.e., a continuous body with a solid core) or may be configured to define an open core rope (i.e., the rope can be tubular with a center axially-extending gap space or opening). Another construct or material may be placed inside the open core rope configuration. The interior construct can be another NDGA treated fiber or NDGA braided fiber construct. The solid rope configuration is believed to more closely correspond to the natural configuration of a tendon.

Typically, the construct 20 is configured to have substantially the same physical thickness and/or configuration as the replaced or repaired tissue so as to not cause discomfort or physical abnormalities in structure.

To form the flat ribbon construct 20$f$, the plurality of fibers 11 in each bundle 10 are arranged to be substantially parallel with each other, and the bundles are woven together in a sequence that interlocks or interlaces them and forms the substantially flat ribbon shape. The weave or braid pattern may also be such so as to allow the construct to be slightly concave to fit over bony structure. For example, between about six to twenty-seven bundles 10 having between about six to thirty fibers each can be braided or woven in a sequence and pattern that produces the substantially flat structure.

Similarly, for the rope configuration 20$r$, the bundles 10 can be configured so that the fibers are offset or parallel, but the weave or braid pattern is such that the bundles interlock to form the substantially tubular rope-like shape. As desired, the body of the construct 20 can include a smooth outer sheath that may be formed by a coating, gel or other material. In particular embodiments, the construct 20 can comprise polyglycolic acid, polylactice acid, or combinations of these or other substances.

The braided or weave pattern can be a relatively tight braid or weave or a relatively loose braid or weave with less structural rigidity and more conformability than a tight weave depending on the target location and the desired mechanical properties and configuration.

In some embodiments, the construct 20 is between about 0.5-50 cm long, typically between about 1-25 cm, and in some embodiments between about 2 cm to about 20 cm long. The construct 20 may have a width that is between about 0.05 to 8 cm, and is typically between about 1-3 cm. The constructs 20 may have a cross-sectional thickness of about 0.01 to about 30 mm. For the flat ribbon construct 20$f$, the thickness may be more typically between about 0.1 to about 10 mm, while the rope construct 20$r$ may have a thicker cross-section, such as between about 5-30 mm.

Figure 5:
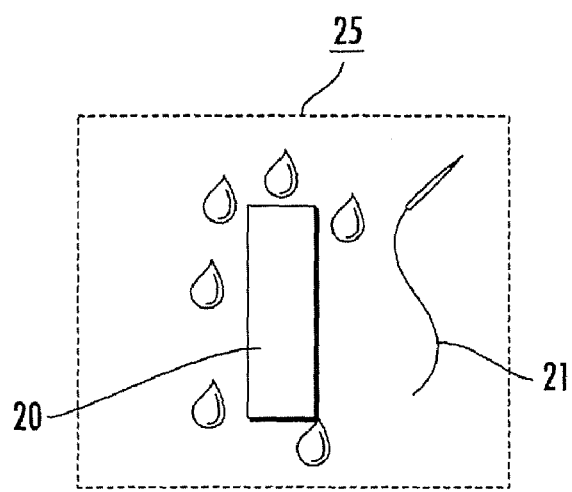
FIG. 5 is a schematic illustration of a medical kit according to embodiments of the invention.

FIG. 5 illustrates a medical kit 25 that includes the construct 20 and may optionally include at least one suture 21, which may be an atraumatic needle with suture. The suture 21 can be a bone anchor suture and/or be configured to cooperate with a bone tunnel as is well-known. The kit 25 may include other components, such as, for example, a container of surgical adhesive and the like. The construct 20 may be held hydrated in a flexible sealed package of sterile liquid. The kit 25 may include a temperature warning so that the construct 20 is not exposed to unduly hot temperatures that may degrade the implant. A temperature sensor may optionally be included on the package of the kit (not shown) to alert the clinician as to any excessive or undue temperature exposure prior to implantation.

FIG. 6A illustrates an example of a construct 20 implanted in a subject according to embodiments of the invention. As shown, the construct is for a ligament repair. One end portion of the construct 20$a$ is attached to a separated portion of the ligament 200 undergoing treatment and the other end portion is attached to the spaced apart portion of the ligament 200 (or bone). As is also shown, the first end portion 20$a$ is attached via a suture 21 and the second end portion 20$b$ is attached using a suture anchor 21$a$. Other anchoring or attachment means may be used. Adhesive 22 may be used to help secure one or both of the end portions 20$a$, 20$b$ during an initial healing phase for additional stabilization.

Figure 6B:
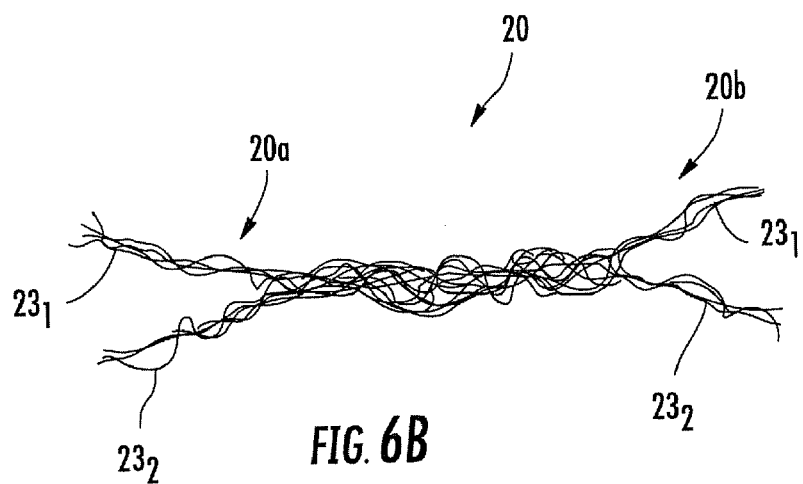
FIGS. 6B and 6C are schematic illustrations of other braided constructs according to embodiments of the invention.
Figure 6C:
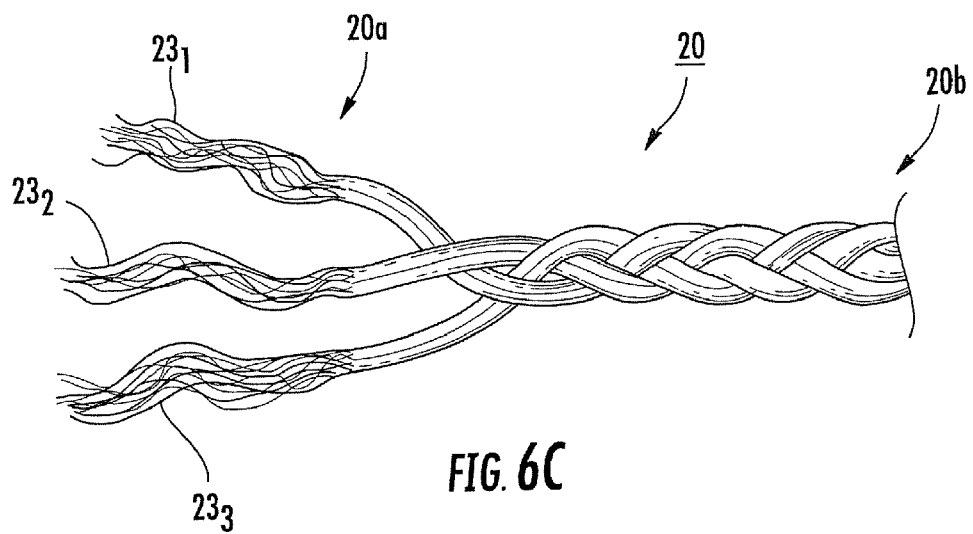

FIGS. 6B and 6C illustrate other embodiments of a construct 20. As shown, at least one end portion (shown as both opposing end portions in FIG. 6B and one end portion in FIG. 6C) can include two or more separations, splits or segments of (tissue or bone) attachment material 23. FIG. 6B illustrates that each end portion 20a, 20b can have the same number of splits or attachment segments 23, shown as two attachment segments $23_1$, $23_2$, on each end portion 20a, 20b. FIG. 6C illustrates that each end portion 20a, 20b can have differing numbers of segments 23, shown as three $23_1$, $23_2$, $23_3$ on first end portion 20a, and no discrete segments on 20b. Each segment may have a different length or the same length on one or both end portions of the construct 20a, 20b. Attachment segments may be formed at other axial or medial locations with or without the end portion attachment segments (not shown). Other numbers of segments 23, configuration of the segments 23 and/or attachment configurations may also be used. Each segment 23 can have differing or the same numbers of fibers or strands 10. The segments 23 can also be formed or treated with fillers, materials or members to increase strength or stabilize anchoring or attachment to inhibit pull out and to secure placement during at least an initial healing phase.

In particular embodiments, such as may be appropriate for a ligament repair, a multi-fiber braid having between about 5-10 bundles of between about 10-100 fibers, such as a 9 bundle, 81 fiber, braided construct 20 can include a plurality of segments 23, with each split or segment 23 having at least about 5 fibers, and typically between 10-80 fibers. In some embodiments, at least two, and typically between three to five, segments 23, (such as about four segments), can be configured on a first and/or second end portion 20a, 20b, and each segment 23 can have between 10-40 fibers, some of which may have between about 10-20 fibers and others may have more than 10, such as between about 30-40 (not shown). In some embodiments, the construct 20 can have between about 10-100 warp fibers or bundles of warp fibers interlaced with one or more weft fiber(s) (see, e.g., FIG. 12).

Figure 7:
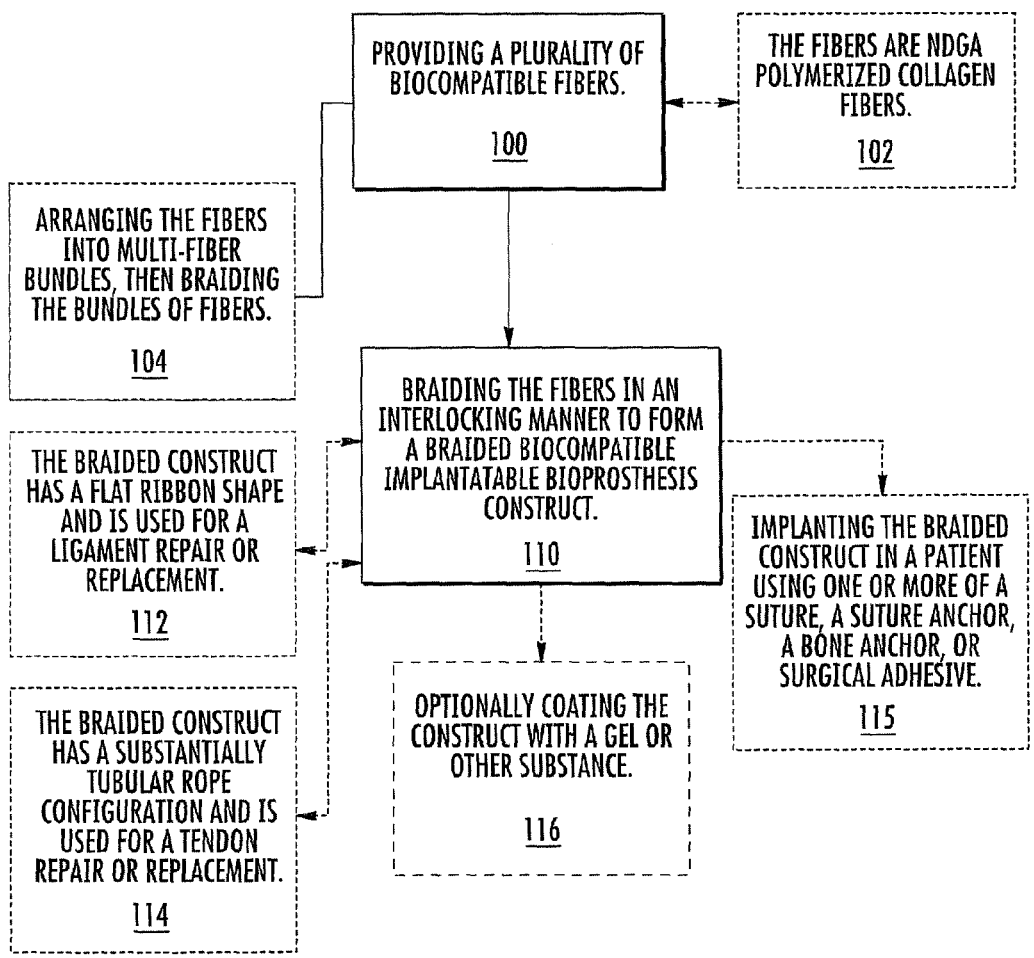
FIG. 7 is a flow chart of operations that can be used to carry out embodiments of the invention.

FIG. 7 illustrates some operations that can be used to carry out embodiments of the invention. As shown, a plurality of biocompatible fibers are provided (block 100). The fibers are braided in an interlocking manner to form a braided biocompatible implantable bioprosthesis construct (block 110).

The fibers may comprise NDGA polymerized collagen fibers (block 102). The fibers can be arranged into bundles of substantially parallel fibers, then the bundles can be braided or woven (block 104). The construct can have a flat ribbon shape and may be used for a ligament repair or replacement (block 112). The construct can have a substantially tubular rope configuration and can be used for a tendon repair or replacement (block 114).

Optionally, the braided and/or woven construct can be implanted in a patient using one or more of a suture, suture anchor, bone anchor, bone tunnel and the like (block 115).

Also, the construct can optionally include, e.g., be coated, impregnated and/or amalgamated with a gel or other material (block 116). The coating may be to promote fibroblasts, and/or comprise one or more of an anti-inflammatory agent, an antibiotic or other therapeutic agent.

The braided and/or woven construct 20 is biocompatible and may be absorbed, resorbed and/or biodegradeable over time.

The constructs 20 can be configured to have similar or greater tensile strength, stiffness and dynamic flexibility as corresponding natural tissue, e.g., natural ligament or tendon fibers. Embodiments of the invention may be particularly suitable for augmenting, repairing or replacing tendons and ligaments.

In some embodiments, the fibers comprise any collagen fibers formed in any suitable manner to be acceptable as a biomedical implant/construct.

In particular embodiments, the fibers can comprise NDGA-treated collagen. Suitable ways of forming NDGA polymerized and/or treated fibers are described in U.S. Pat. Nos. 6,565,960 and 6,821,530, the contents of which are hereby incorporated by reference as if recited in full herein. Generally stated, bulk collagen can be solubilized by digestion with a protease, then extruded into a synthetic fiber. Properly processed NDGA polymerized fibers are biocompatible. After the polymerization process, the fibers can be washed in ethanol and phosphate buffered saline to remove cytotoxins due to leachable reaction products.

Figure 8A:
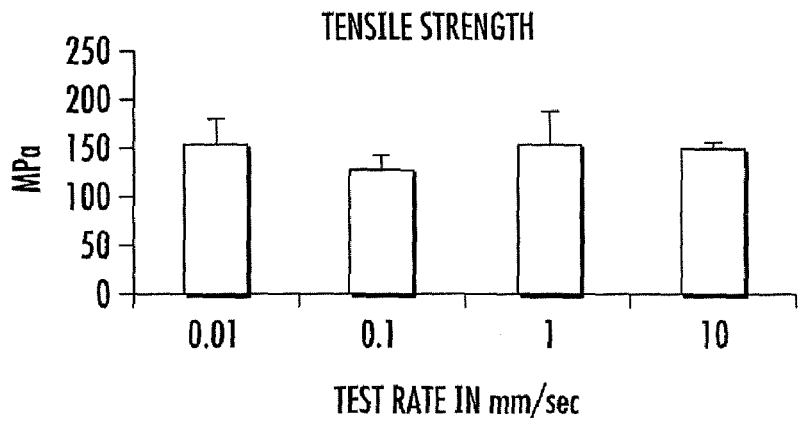
FIG. 8A is a graph of tensile strength of NDGA fibers of different fibers showing strength (MPa) versus test rate in mm/sec.
Figure 8B:
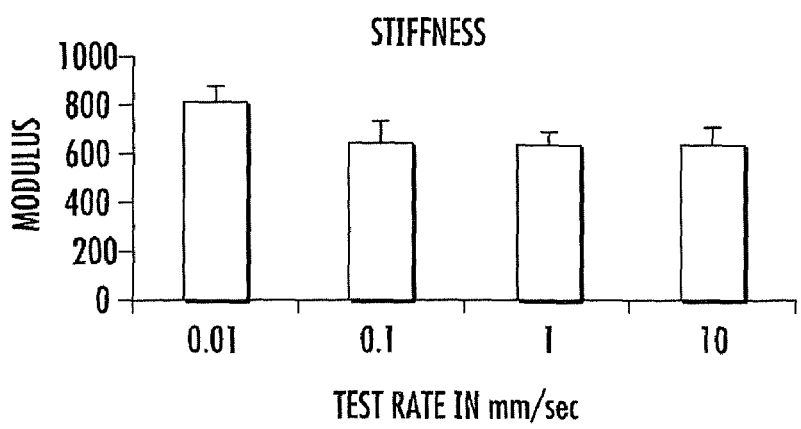
FIG. 8B is a graph of stiffness of NDGA fibers of different fibers showing modulus versus test rate in mm/sec.
Figure 8C:
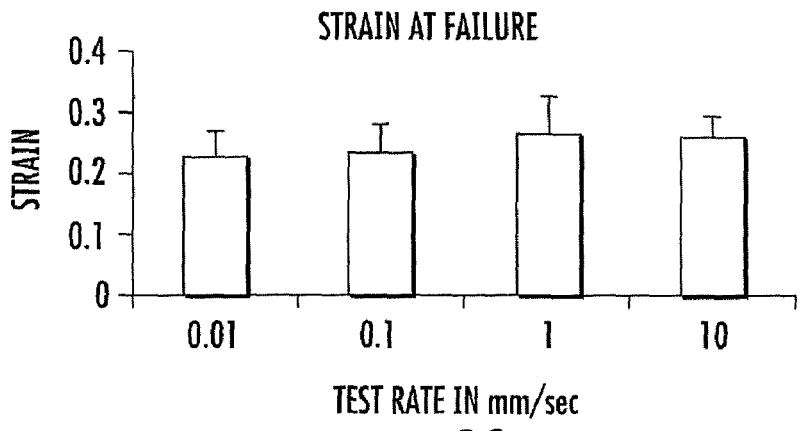

As has been established by the inventors, NDGA-treated collagen fibers are biocompatible and have desirable mechanical properties. FIGS. 8A-8C illustrate different strain rates indicating that the fibers are nearly elastic in tension; i.e., strain rate independent. The fibers were mounted in clamps with 2 cm nominal tested length. Fibers were deformed to failure. The linear portion of the stress/strain curve was used to calculate the elastic modulus (stiffness) and the force at which the fibers failed was normalized to cross sectional area yielding tensile strength. Values shown are means+/−S.D. for six specimens. For additional discussion of the NDGA polymerized fibers, see, Thomas J. Koob, *Biomimetic approaches to Tendon Repair*, Comparative Biochemistry and Physiology Part A 133 (2002) 1171-1192. The braided or woven constructs 20 using fibers of this type can provide even stronger bioprostheses.

The bundles 10 can be formed with fibers having widths in any suitable range, typically in the range of between about 0.01-10 mm. One or more of the fibers 11 in a bundle 10 may be continuous or discontinuous over its length or may terminate before the end of the construct 20.

Figure 9:
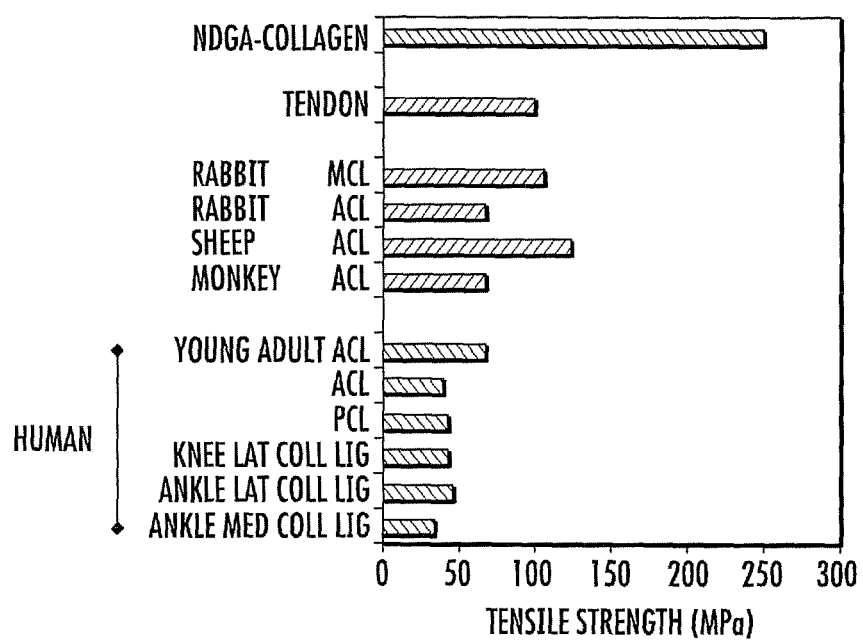
FIG. 9 is a graph of tensile strength (MPa) of NDGA collagen fibers and other natural tendons and ligaments according to embodiments of the invention.

FIG. 9 is a graph of tensile strength (MPa) of NDGA collagen fibers and other natural tendons and ligaments according to embodiments of the invention. As shown, the NDGA collagen fibers may, in some embodiments, be high-strength. The term "high-strength" refers to fibers having an average tensile strength of at least about 150 MPa, such as between about 180 MPa and 350 MPa, and typically, for bovine, porcine or caprine based "donor" collagen, between about 180 MPa and 280 MPa, such as between about 240-279 MPa (measured on average). The fibers may also have suitable stiffness and strain yield. In general, the fibers can have a stiffness of at least about 200 MPa (e.g., at least about 300, 400, 500, or 600 MPa), and a strain at failure of less than about 20% (e.g., less than about 15 or 10%). The fibers may be formed with a relatively thin diameter, such as, for example about a 0.08 mm dry diameter (on average) and about a 0.13 mm wet diameter (on average).

To make the collagen fibers, preparatory donor collagen material can be pepsin-derived or solubilized collagen that is processed/purified. The purified collagen preparatory material is dialyzed a plurality of times in a selected liquid for a desired period of time. The dialyzing is typically repeated three times. The dialyzing can be carried out against dionized (DI) water in a volume ratio of between about 30:1 to about 100:1, typically about 60 to 1, for between about 30-90 minutes, typically about 40 minutes. The dialyzing can form a substantially clear gel of collagen fibrils indicating good organization (substantially parallel fibrils), where opacity indicates less organization. The organization can help improve tensile strength of subsequently cross-linked fibers.

The dialyzed collagen material can be incubated for a desired time before placing in a fiber-forming buffer. The dialyzed gel can be cross-linked to provide collagen fibers for medical constructs. The polymerization (e.g., cross-linking) can be carried out using NDGA and the resultant NDGA treated collagen fibers can be relatively thin, such as, for example, about 0.08 mm dry diameter (on average).

The incubation may be for at least about 24 hours, typically 24-48 hours, and may be at room temperature of between about 15-30° C., typically about 25° C. The dialysis process can be used before cross-linking for subsequent use with any suitable cross-linking materials, to promote collagen organization, such as, for example, and the process is not limited to NDGA, but may be useful with other materials, including, for example, glutaraldehyde. For additional discussion of methods used to form high-strength NDGA treated collagen fibers, see, U.S. Provisional Application Ser. No. 60/883,408, and/or its corresponding regular utility counterpart, the contents of which are hereby incorporated by reference as if recited in full herein.

The present invention is explained in greater detail in the following non-limiting Examples.

EXAMPLES

Figure 10:
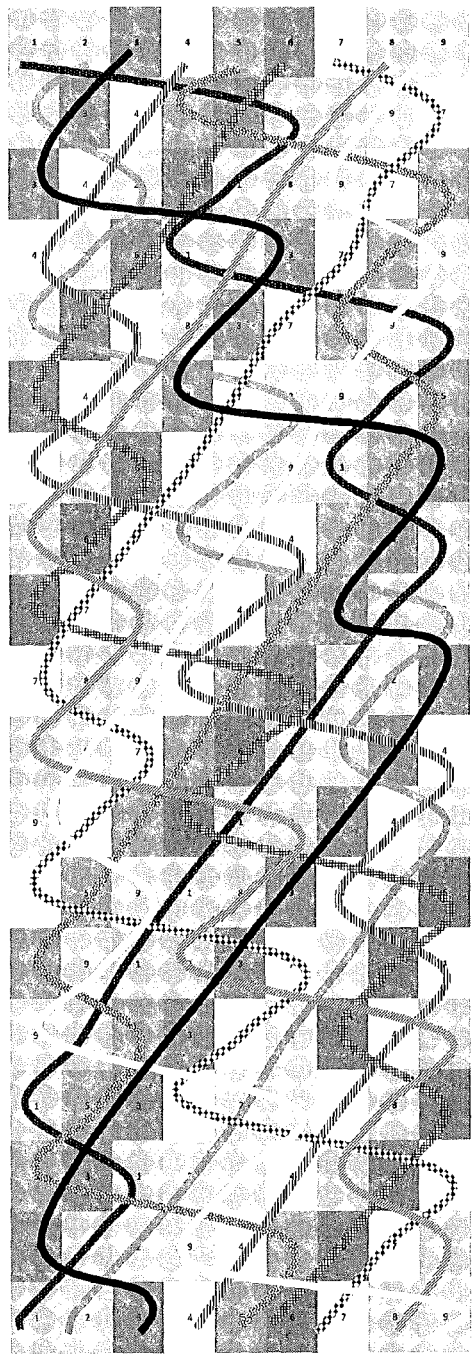
FIG. 10 is a schematic illustration of a braiding pattern using nine bundles of nine parallel fibers, each forming an interlocking braid, using the sequence shown according to embodiments of the invention. The nine bundles are numbered and include distinct shading/patterns to aid in identification. The interlocking bundle in each round of braiding is alternately shown as either bold or underlined (e.g., bundle #1 is the interlocking strand in round 1, whilst bundle #5 is the interlocking strand in round 2). As shown, the nine bundles return to their original position as braiding progresses to round 18, at which point the braiding pattern may repeat.
Figure 11:
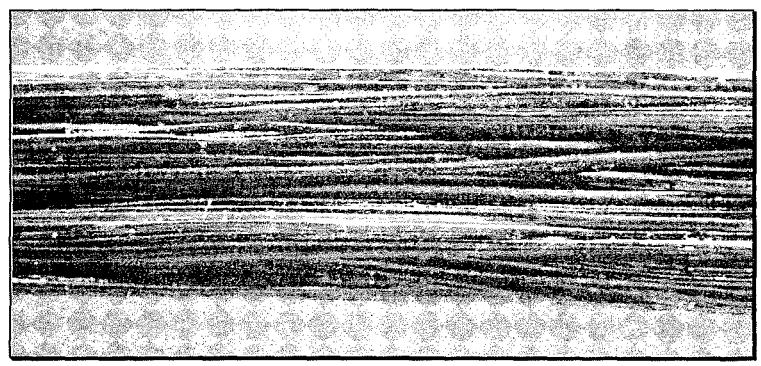
FIG. 11 is a digital image of the 81-fiber braided ribbon formed by the pattern shown in FIG. 10 according to embodiments of the invention.

Eighty-one NDGA-collagen fibers were braided as 9 bundles of 9 parallel fibers each, as shown in FIGS. 10 and 11, and coated with gelatin for increased stability during handling. The size of this ribbon is 2.3×0.9×25 cm. The ribbon was used in an ex vivo evaluation of a thumb ulnar collateral ligament.

FIG. 10 illustrates the braiding method/configuration used to form the 81 fiber ribbon. FIG. 11 illustrates the actual braided NDA-collagen ribbon used for the ligament repair.

The goal was to create a prosthesis for thumb ulnar collateral ligament (UCL) reconstruction that is biocompatible, affords sufficient strength to allow early mobility motion protocols that provides a scaffold for native tissue ingrowth.

A collateral ligament bioprosthesis was designed using braided collagen fibers polymerized with NDGA. Ten fresh-frozen adult cadaver forearms were randomized into three treatment groups to test various methods of fixation of thumb UCL repair. All repairs were secured to bone using Mini-Mitek suture anchors and 2-0 repair. All repairs were secured to bone using Mini-Mitek suture anchors and 2-0 Ethibond. Three were directly repaired with anchors following sharp transaction, three were reconstructed using a palmaris graft through drill holes distally and an anchor proximally, and four were reconstructed using the NDGA bioprosthesis. All specimens were dissected and tested using a previously validated biomechanical model for this ligament.

The direct repair group failed at a mean of 43N, the palmaris reconstruction group at a mean of 38N, and the NDGA-bioprosthesis at a mean of 227N. In the direct repair group, two specimens failed at the suture-ligament interface and one by anchor pull-out. In the palmaris group, one failed at the bone tunnel distally, one at the suture knot, and one anchor failure upon implantation. In the NDGA group, two failed at the bone-anchor interface and two at the NDGA-suture interface. The data for the direct repair and palmaris groups is consistent with previously reported measurements.

Figure 12:
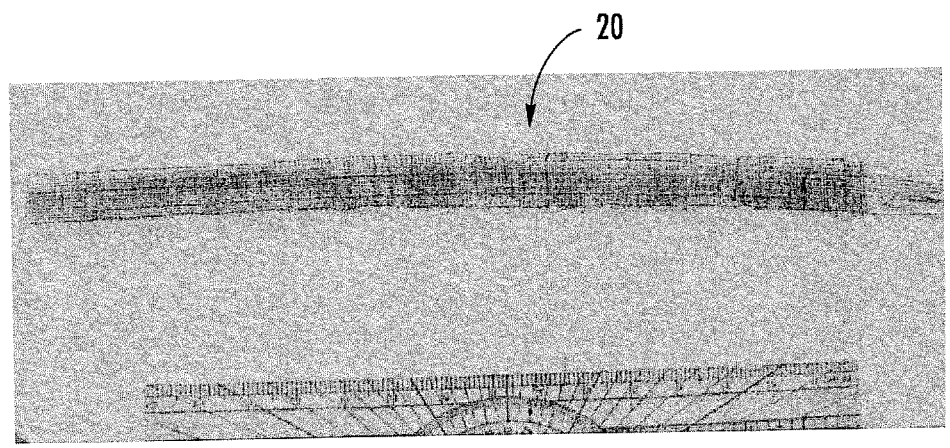
FIG. 12 is a digital image of a top view of a single layer woven multi-fiber prosthesis according to embodiments of the present invention.
Figures 13A, 13B:
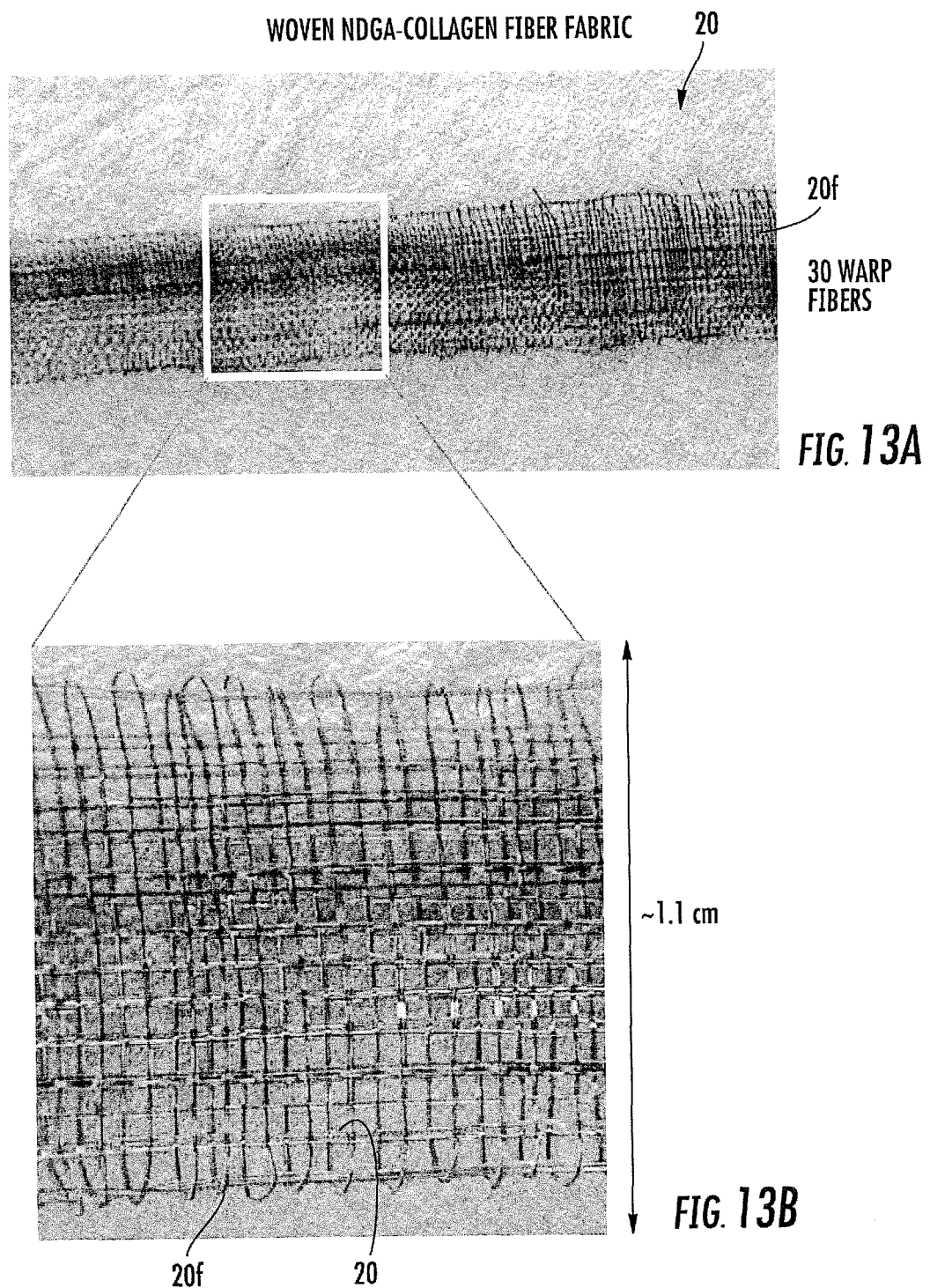
FIG. 13A is a digital image of an enlarged view of a portion of the prosthesis shown in FIG. 12.
FIG. 13B is a digital image of a greatly enlarged view of a portion of the prosthesis shown in FIG. 12.

FIGS. 12, 13A and 13B show an alternate example of a woven prosthesis 20. This prototype was made using 30 warp fibers of woven NDGA-collagen fiber to create a woven fabric having a width of about 1.1 cm and a length of about 15 cm. The prototype is a substantially planar, single-layer woven prosthesis of high-strength NDGA-treated collagen fibers. Embodiments of the invention contemplate that there is a large range of alternate dimensions, thread or fiber count, numbers of layers, weave design, and the like.

Previous studies using animal models have confirmed the biocompatibility of these NDGA fibers, as well as the attachment, proliferation, and migration of reparative fibroblasts to these fibers. Reconstruction of the thumb UCL with an NDGA-collagen prosthesis afforded strength approaching an order of magnitude higher than that obtained by the clinical standard of care repair when tested under a validated biomechanical model and exceeds published acceptable strength for allowance of controlled active motion therapy protocols. The prosthetic ligament did not fail in these ex vivo tests; instead, the device failed at either the bone anchor or suture attachment. Given the biocompatibility, the excellent biomechanical properties and the potential for biologic in growth of native tissue for long-term stability, this prosthetic NDGA construct offers a unique potential for future collateral ligament reconstruction.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. An implantable bioprosthesis, comprising:
an implantable construct consisting essentially of a plurality of NDGA polymerized collagen fibers, wherein the NDGA polymerized collagen fibers have a tensile strength that is between about 180-350 MPa and are arranged into bundles of substantially parallel fibers, with each of the bundles comprising at least two NDGA polymerized collagen fibers, wherein the bundles are braided and woven or braided or woven together, and wherein the construct has tensile strength, stiffness and dynamic flexibility that meets or exceeds that of a pre-injury natural ligament or tendon.

2. A bioprosthesis according to claim 1, wherein the NDGA polymerized collagen fibers are arranged into at least three bundles.

3. A bioprosthesis according to claim 1, wherein the NDGA polymerized collagen fibers are arranged into between about six to about twenty-seven bundles.

4. A bioprosthesis according to claim 1, wherein the NDGA polymerized collagen fibers are arranged into nine.

5. A bioprosthesis according to claim 1, wherein at least some of the bundles comprise between about 6 to about 11 fibers.

6. A bioprosthesis according to claim 1, wherein each bundle comprises nine NDGA polymerized collagen fibers.

7. A bioprosthesis according to claim 1, wherein the fibers in each bundle abut each other.

8. A bioprosthesis according to claim 1, wherein the construct is between about 1-25 cm long.

9. A bioprosthesis according to claim 7, wherein the construct is between about 0.1 cm to about 3 cm wide.

10. A bioprotheis according to claim 1, wherein the construct has a substantially flat ribbon configuration sized and configured for a ligament or tendon repair.

11. A bioprostheis according to claim 10, wherein the bioprothesis is an ACL bioprosthesis.

12. A bioprostheis according to claim 1, wherein the construct has a substantially tubular rope configuration sized and configured to define a tendon bioprosthesis.

13. A bioprosthesis according to claim 12, wherein the tendon bioprosthesis is a flexor tendon bioprosthesis.

14. A bioprosthesis according to claim 10, wherein the construct is a ligament implant that has a tensile strength, stiffness and dynamic flexibility that meets or exceeds that of the corresponding natural ligament it is used to augment, repair and/or replace.

15. A bioprosthesis according to claim 12, wherein the construct is a tendon implant that has a tensile strength, stiffness and dynamic flexibility that meets or exceeds that of the corresponding natural tendon it is used to augment, repair and/or replace.

16. A bioprosthesis according to claim 1, wherein the construct includes a gel coating for defining a smooth outer sheath and/or for promoting fibroblasts.

17. A bioprosthesis according to claim 1, wherein at least one end portion of the construct includes at least two split segments of fibers that are configured as bone or tissue attachment segments.

18. A medical kit for a tendon or ligament repair, augmentation or replacement, comprising: a construct consisting essentially of elongate high-strength NDGA polymerized collagen fibers, wherein the elongate high-strength NDGA polymerized collagen fibers have a tensile strength that is between about 180-350 MPa and are arranged into bundles of substantially parallel fibers, wherein the bundles are braided and woven or braided or woven together, and wherein the construct has tensile strength, stiffness and dynamic flexibility that meets or exceeds that of a pre-injury natural ligament or tendon; and a sterile package sealably enclosing the braided or woven fiber construct therein.

19. A medical kit according to claim 18, wherein the construct has a substantially flat configuration.

20. A medical kit according to claim 19, wherein the construct is a bioprosthesis ligament or tendon for a respective ligament or tendon repair, augmentation or replacement.

21. A medical kit according to claim 18, wherein the construct has a substantially tubular braided rope configuration and is a bioprosthesis for a tendon repair, augmentation or replacement.

22. A bioprosthesis according to claim 1, wherein substantially all of the fibers are sized to have about a 0.08 mm dry diameter (on average) and about a 0.13 mm wet diameter (on average).

23. A bioprosthesis according to claim 1, wherein the fibers have a substantially common size and all of the fibers are NDGA polymerized collagen fibers.

24. A bioprosthesis according to claim 1, wherein the fibers have a tensile strength that is between about 180-280 MPa.

25. A medical kit according to claim 18, wherein the package comprises a temperature sensor for indicating whether the construct in the package has been exposed to an undesired temperature prior to use.

26. An implant, comprising:
an implantable construct consisting essentially of 81 NDGA-polymerized collagen fibers having a tensile strength that is between about 180-350 MPa and substantially the same diameter, wherein the with 81 fibers are arranged as nine bundles of nine parallel fibers each, wherein each bundle is represented by a corresponding number 1, 2, 3, 4, 5, 6, 7, 8, and 9, respectively, and wherein the nine bundles have a repeating braid pattern defined by the following sequence:
2 3 4 5 6 1 8 9 7
3 4 2 6 1 8 9 7 5
4 2 6 1 8 3 7 5 9
2 6 4 8 3 7 5 9 1
6 4 8 3 7 2 9 1 5
4 8 6 7 2 9 1 5 3.

27. A medical kit according to claim 18, wherein the construct has 81 fibers arranged as nine bundles of nine parallel fibers each, wherein each bundle is represented by a corresponding number 1, 2, 3, 4, 5, 6, 7, 8, and 9, respectively, and wherein the nine bundles have a repeating braid pattern defined by the following sequence:
2 3 4 5 6 1 8 9 7
3 4 2 6 1 8 9 7 5
4 2 6 1 8 3 7 5 9
2 6 4 8 3 7 5 9 1
6 4 8 3 7 2 9 1 5
4 8 6 7 2 9 1 5 3.

28. A bioprosthesis according to claim 27, wherein the construct is sized and configured for a thumb ulnar collateral ligament reconstruction.

29. A bioprosthesis according to claim 1, wherein the construct is a flat woven construct having a cross-fiber weave pattern with some of the fibers extending in a longitudinal direction and other of the fibers woven through the longitudinally extending fibers in a transverse direction that is substantially orthogonal to the longitudinal direction.

30. A medical kit according to claim 18, wherein the construct is a flat woven construct having a cross-fiber weave pattern with some of the fibers extending in a longitudinal direction and other of the fibers woven through the longitudinally extending fibers in a transverse direction that is substantially orthogonal to the longitudinal direction.

31. A bioprostheis according to claim 1, wherein each bundle of fibers is defined by a group of adjacent fibers with a length that is between about 1-25 cm, wherein the number of fibers in a respective bundle is between about 10 to about 100, and wherein the number of bundles is between about 5 to about 10.

32. A medical kit according to claim 18, wherein each bundle of fibers is defined by a group of adjacent fibers with a length that is between about 1-25 cm, wherein the number of fibers in a respective bundle is between about 6 to about 30, and wherein the number of bundles is between about 6 to about 27.

33. A bioprosthesis according to claim 1, wherein all the fibers in the construct have substantially the same width that is between about 0.01 mm to about 10 mm, and wherein the construct is substantially flat.

34. A medical kit according to claim 18, wherein the bundles are woven together to form a single layer substantially planar construct, and wherein the construct has between about 10-100 bundles of warp fibers interlaced with one or more weft fibers.

35. A bioprosthesis according to claim 1, wherein substantially all of the fibers are sized to have a fiber width between about a 0.01 mm to about 10 mm.

36. A bioprosthesis according to claim 35, wherein all of the fibers have a substantially common size.

37. An implant comprising NDGA-polymerized collagen fibers having a tensile strength that is between about 180-350 MPa arranged as nine bundles, wherein each bundle is represented by a corresponding number 1, 2, 3, 4, 5, 6, 7, 8, and 9, respectively, and wherein the nine bundles have a repeating braid pattern defined by the following sequence:

2 3 4 5 6 1 8 9 7
3 4 2 6 1 8 9 7 5
4 2 6 1 8 3 7 5 9
2 6 4 8 3 7 5 9 1
6 4 8 3 7 2 9 1 5
4 8 6 7 2 9 1 5 3.

38. A medical kit according to claim 18, wherein the bundles are nine bundles of substantially parallel fibers, wherein each bundle is represented by a corresponding number 1, 2, 3, 4, 5, 6, 7, 8, and 9, respectively, and wherein the nine bundles have a repeating braid pattern defined by the following sequence:
2 3 4 5 6 1 8 9 7
3 4 2 6 1 8 9 7 5
4 2 6 1 8 3 7 5 9
2 6 4 8 3 7 5 9 1
6 4 8 3 7 2 9 1 5
4 8 6 7 2 9 1 5 3.

39. A bioprostheis according to claim 1, wherein the construct has a substantially flat ribbon shape and is configured to be slightly concave to fit over boney structure in an implanted position.

40. A bioprosthesis according to claim 10, wherein the construct bundles of fibers are woven together and define a planar single layer construct configured for collateral ligament reconstruction.

41. A bioprosthesis according to claim 1, wherein the construct has a loose braid or weave pattern.

42. A bioprosthesis consisting essentially of NDGA polymerized collagen fibers, wherein the NDGA polymerized collagen fibers have a tensile strength that is between about 180-350 MPa and are arranged as about 10 to about 100 bundles of substantially parallel warp fibers and one or more weft fibers, wherein each bundle of warp fibers comprises at least two NDGA polymerized collagen fibers, and wherein the bundles of warp fibers and the one or more weft fibers are woven together to form a single-layer substantially planar construct.

43. A bioprosthesis comprising NDGA polymerized collagen fibers, wherein the NDGA polymerized collagen fibers have a tensile strength that is between about 180-350 MPa and are arranged as about 10 to about 100 bundles of substantially parallel warp fibers and one or more weft fibers, wherein each bundle of warp fibers comprises at least two NDGA polymerized collagen fibers, and wherein the bundles of warp fibers and the one or more weft fibers are woven together to form a single-layer substantially planar construct.

\* \* \* \* \*

UNITED STATES PATENT AND TRADEMARK OFFICE
CERTIFICATE OF CORRECTION

PATENT NO. : 8,177,839 B2  
APPLICATION NO. : 11/964745  
DATED : May 15, 2012  
INVENTOR(S) : Koob et al.

Page 1 of 1

It is certified that error appears in the above-identified patent and that said Letters Patent is hereby corrected as shown below:

On Title Page: item (56):
Page 2, Other Publications, right column, line 41: "Koob et al.":
Please correct "vitro, @ 2001 John Wiley & Sons, Inc."
to read -- vitro, © 2001 John Wiley & Sons, Inc. --

In the Claims:
Column 10, Claim 1, Line 42:
Please correct "braided and woven or braided or woven together,"
to read -- braided or woven or braided and woven together, --

Claim 4, Line 53: Please correct "fibers are arranged into nine."
to read -- fibers are arranged into nine bundles. --

Column 11, Claim 18, Line 33:
Please correct "and woven or braided or woven together,"
to read -- or woven or braided and woven together, --

Claim 26, Line 64: Please correct "diameter, wherein the with 81 fibers"
to read -- diameter, wherein the 81 fibers --

Signed and Sealed this  
Thirteenth Day of November, 2012

David J. Kappos  
*Director of the United States Patent and Trademark Office*